United States Patent [19]

Nakano et al.

[11] Patent Number: 4,731,375
[45] Date of Patent: Mar. 15, 1988

[54] COUMARIN DERIVATIVES AND ANTIALLERGIC AGENTS CONTAINING THE SAME

[75] Inventors: Jun Nakano, Moriyama; Toshikazu Awaji, Shiga; Kiyoshi Kuriyama, Takatsuki; Yoshiyuki Hiyama, Otsu; Toshiaki Okuda, Kusatsu, all of Japan

[73] Assignee: Kaken Pharmaceutical Co., Ltd., Tokyo, Japan

[21] Appl. No.: 806,917

[22] Filed: Dec. 9, 1985

[30] Foreign Application Priority Data

Dec. 10, 1984 [JP] Japan ................. 59-261039

[51] Int. Cl.⁴ .................... A61K 31/41; C07D 257/04
[52] U.S. Cl. .................................... 514/381; 548/253
[58] Field of Search ..................... 548/253; 514/381

[56] References Cited

U.S. PATENT DOCUMENTS 3,600,437 8/1971 Marshall .................... 548/252
4,406,908 11/1983 Matsuda et al. ............ 548/253

*Primary Examiner*—Glennon H. Hollrah
*Assistant Examiner*—D. B. Springer
*Attorney, Agent, or Firm*—Armstrong, Nikaido, Marmelstein & Kubovcik

[57] ABSTRACT

A chromene derivative having the general formula (I):

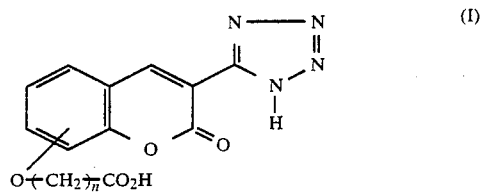

wherein n is 1 to 5 and $-(O-CH_2)_n-CO_2H$ group is attached to 5-position, 6-position, 7-position or 8-position, or salts thereof, a process for preparing the same and antiallergic agents containing the same.

The compounds of the present invention inhibit the immunological release of chemical mediators such as SRS-A and histamine from mast cell and have an excellent effect in preventing and treating the various allergic diseases such as allergic asthma, allergic dermatitis, allergic nasitis, hives, allergic enteritis and allergic conjunctivitis, especially allergic asthma.

16 Claims, No Drawings

COUMARIN DERIVATIVES AND ANTIALLERGIC AGENTS CONTAINING THE SAME

BACKGROUND OF THE INVENTION

The present invention relates to a chromene derivative, a process for preparing the same and antiallergic agent containing the same as an active principle.

It was found by the present inventors that some compound showed strong antiallergic activity, the compound being present in the metabolic products obtained when administering to mammalian animals some kind of coumarin derivatives having the general formula (III):

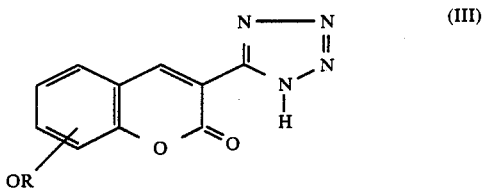

wherein R is alkyl group having 1 to 20 carbon atoms or alkenyl group having 2 to 20 carbon atoms and OR group is attached to 5-position, 6-position, 7-position or 8-position of the coumarin ring, which is described in Japanese Unexamined Patent Publication Nos. 76873/1980 and 71087/1981. As the result of the continuous efforts of the present inventors to obtain the compound useful for antiallergic agents, it has now been found that, among the compound having the general formula (III) wherein OR group is alkyloxy group, the compound of the general formula (III) wherein the end carbon of the corresponding alkyl side chain is carboxyl group has a strong antiallergic activity, low toxicity and high safety.

SUMMARY OF THE INVENTION

Namely, the present invention relates to a chromene derivative having the general formula (I):

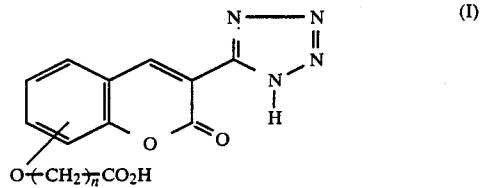

wherein n is 1 to 5 and $-O-(CH_2)_n-CO_2H$ group is attached to 5-position, 6-position, 7-position or 8-position, or salts thereof, a process for preparing the same and antiallergic agents containing the same.

DETAILED DESCRIPTION

An alkanoic acid corresponding to the $(CH_2)_n CO_2H$ group in the above-mentioned formula (I) is a linear alkanoic acid having 2 to 6 carbon atoms such as, for instance, acetic acid, propionic acid, butyric acid, pentanoic acid and hexanoic acid. Salts of the compound having the general formula (I) include pharmaceutically acceptable salts such as addition salt with ammonia or amine such as ethanolamine, ethylamine, diethylamine, triethylamine, diisopropylamine and metal salt such as sodium, potassium, aluminium and calcium salts. Examples of the suitable compounds of the present invention are, for instance, [2-oxo-3-(1H-tetrazole-5-yl)-2H-chromene-8-yloxy]acetic acid, [2-oxo-3-(1H-tetrazole-5-yl)-2H-chromene-6-yloxy]acetic acid, 4-[2-oxo-3-(1H-tetrazole-5-yl)-2H-chromene-8-yloxy]butyric acid, 4-[2-oxo-3-(1H-tetrazole-5-yl)-2H-chromene-7-yloxy]butyric acid, 4-[2-oxo-3-(1H-tetrazole-5-yl)-2H-chromene-6-yloxy]butyric acid, 4-[2-oxo-3-(1H-tetrazole-5-yl)-2H-chromene-5-yloxy]butyric acid, 6-[2-oxo-3-(1H-tetrazole-5-yl)-2H-chromene-8-yloxy]-hexanoic acid, 6-[2-oxo-3-(1H-tetrazole-5-yl)-2H-chromene-7-yloxy]-hexanoic acid, 6-[2-oxo-3-(1H-tetrazole-5-yl)-2H-chomene-6-yloxy]hexanoic acid, 6-[2-oxo-3-(1H-tetrazole-5-yl)-2H-chromene-5-yloxy]hexanoic acid, and the like, and salts thereof.

The compound having the general formula (I) of the present invention can be prepared by reacting 3-cyanochromene derivative having the formula (II):

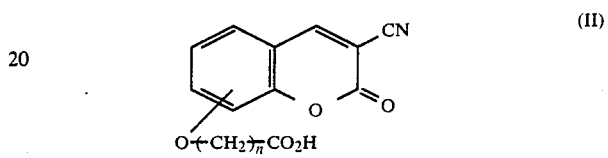

wherein n and the position of the $-O-(CH_2)_n CO_2H$ group are as above, with hydrazoic acid or a salt thereof. Examples of the salt of hydrazoic acid employed in the reaction are, for instance, alkali metal salts such as lithium azide, sodium azide and potassium azide; alkaline earth metal salts such as magnesium azide, calcium azide, barium azide and strontium azide; other metal salts such as aluminium azide, tin azide, zinc azide and titanium azide; salts with an organic base such as ammonium azide and anilinium azide; and the like. Such salts of hydrazoic acid may be employed alone, or alkali metal salt such as sodium azide may be employed in combination with a Lewis acid such as aluminium chloride, stannic chloride, zinc chloride or titanium tetrachloride, or ammonium chloride. When the alkali metal salt is employed in combination with a Lewis acid, the salt is reacted with the Lewis acid to form the salt of hydrazoic acid such as aluminium azide, tin azide, zinc azide, titanium azide or ammonium azide, which is then reacted with 3-cyanochromene derivative having the general formula (II). A combination of the alkali metal salt of the hydrazoic acid and the above-mentioned Lewis acid provides particularly satisfactory result. The amount of hydrazoic acid, salt thereof and Lewis acid usually ranges from around 1 to around 10 mole per one mole of 3-cyanochromene derivative having the general formula (II).

The reaction is generally carried out in an organic solvent. Examples of the solvent are, for instance, hydrocarbons such as benzene, toluene and petroleum ether; ethers such as tetrahydrofuran, dioxane and ethyl ether; polar aprotic solvent such as diemthylformamide and dimethylsulfoxide; and the like. Though the reaction temperature and the reaction time are not particularly limited, the reaction may usually be carried out at the temperature ranging from around room temperature to around 130° C. for around 30 minutes to around 100 hours. When the salt of hydrazoic acid is employed in the above-mentioned reaction, a desired compound is produced in the form of a salt corresponding to the salt of hydrazoic acid employed in the reaction due to the acidity of the tetrazolyl group. The obtained salt may be isolated as it is, or treated with mineral acid such as hydrochloric acid or sulfuric acid to form the desired compound (I) having a free tetrazolyl group. Isolation or purification of the compound of the present invention can be carried out by a conventional method such as chromatography or recrystallization. Though the salt of the compound having the general formula (I) can be prepared directly by the above-mentioned reaction in some cases, the salt may be prepared by isolating the compound (I) and then reacting it with the corresponding base.

In the above-mentioned reaction, 3-cyanochromene derivatives having the general formula (II) as a starting material in the present invention are all new compounds. The novel 3-cyanochromene derivatives having the general formula (II) can be obtained by the process (A), process (B) or process (C) as follows:

[process (A)]

A salicylaldehyde derivative having the general formula (IV):

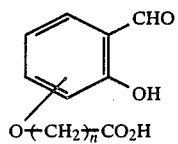

wherein n is as above and the $-O-(CH_2)_n-CO_2H$ group is attached at 3-position, 4-position, 5-position or 6-position of salicylaldehyde, is reacted with malononitrile or a cyanomalonic acid ester (for instance, a lower alcohol ester such as methyl ester or ethyl ester) in a lower alcohol or water-containing lower alcohol as a solvent in the presence of a catalytic amount of an inorganic base such as sodium hydrogencarbonate, sodium carbonate, sodium hydroxide, potassium fluoride or potassium carbonate or an organic base such as piperidine, pyrrolidine, ammonia or triethylamine to produce the desired compound. The reaction is carried out at 0° to 100° C. for 30 seconds to 5 hours.

[Process (B)]

A 3-cyanochromene derivative having the general formula (V):

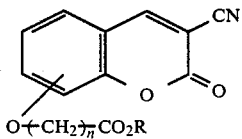

wherein n is as above, R is a lower alkyl group such as methyl group or ethyl group and the $-O-(CH_2)_n-CO_2R$ group is attached at 5-position, 6-position, 7-position or 8-position of the chromene ring, dissolved in methylene chloride or chloroform is reacted with tetrahydrothiophene or dimethyl sulfide in the presence of anhydrous aluminium bromide at $-20°$ to 80° C. for 15 minutes to 24 hours. Alternatively, 3-cyanochromene derivative having the general formula (V) is reacted with trimethylsilane iodide or trimethylsilane chloride in acetonitrile as a solvent in the presence of sodium iodide at 0° to 100° C. for 30 minutes to 48 hours.

[Process (C)]

A 3-cyanochromene derivative having the general formula (V) is hydrolyzed with an aqueous solution of inorganic base such as sodium hydroxide or potassium hydroxide in a lower alcohol such as methanol or ethanol as a solvent at 0° to 40° C. for 3 minutes to 1 hour.

The compounds of the present invention are used with complete safety as antiallergic agents, which can be administered by oral route in the form of tablets, capsules, powders or granules or can be used as snuff in the form of powder, or as aerosols in the form of solution or dispersion. Also the compounds of the present invention show excellent activities as external preparations and is used as ointments or cataplasm. The compounds of the present invention in the form of salt are soluble in water and can be used as injections, syrup, nasal drops or eye drops. Effective dose for man of the compounds of the present invention is around 0.05 to around 200 mg/day. Pharmaceutical preparation of the compounds of the present invention is not particularly limited and can be carried out in accordance with the conventional technique using the conventional carriers such as binder, solid diluent, liquid diluent and filling material, more particularly such as starch, lactose, microcrystalline cellulose, sucrose, magnesium stearate, anhydrous silic acid, talc, physiological saline, and the like.

The compounds of the present invention inhibit the immunological release of chemical mediators such as SRS-A and histamine from mast cell and have an excellent effect in preventing and treating the various allergic diseases such as allergic asthma, allergic dermatitis, allergic rhinitis, hives, allergic enteritis and allergic conjunctivitis, especially allergic asthma. For example, 4-[2-oxo-3-(1H-tetrazole-5-yl)-8-chromenyloxy]butyric acid showed an inhibitory effect in high degree in the experiment employing experimental asthma model of animals. The compounds of the present invention, as already mentioned, can be used in any administration forms such as oral administration, injection and percutaneous absorption.

The present invention is more particularly described by the following test Examples, Reference Examples and Examples. However, it should be understood that the present invention is not limited to these Test Examples, Reference Examples and Examples.

Fifty % inhibitory dose ($ID_{50}$) in Passive Cutaneous Anaphylaxis (PCA) test in rat (Test Example 1) and Minimal Lethal Dose (MLD) in intraperitoneal acute toxicity test in mouse (Test Example 2) were determined for the typical compounds of the present invention as follows:

[2-oxo-3-(1H-tetrazole-5-yl)-2H-chromene-8-yloxy]acetic acid (Compound A),

4-[2-oxo-3-(1H-tetrazole-5-yl)-2H-chromene-8 yloxy]-butyric acid (Compound B),

4-[2-oxo-3-(1H-tetrazole-5-yl)-2H-chromene-6-yloxy]-butyric acid (Compound C);

6-[2-oxo-3-(1H-tetrazole-5-yl)-2H-chromene-8-yloxy]-hexanoic acid (Compound D),

6-[2-oxo-3-(1H-tetrazole-5-yl)-2H-chromene-7-yloxy]-hexanoic acid (Compound E),

6-[2-oxo-3-(1H-tetrazole-5-yl)-2H-chromene-6-yloxy]-hexanoic acid (Compound F),

6-[2-oxo-3-(1H-tetrazole-5-yl)-2H-chromene-5-yloxy]-hexanoic acid (Compound G)

TEST EXAMPLE 1

The antiallergic activities of the chromene derivatives of the present invention were tested in passive cutaneous anaphylaxis (hereinafter referred to as "PCA") by homocytotropic antibody (hereinafter referred to as "HTA").

Method (1) Preparation of antiserum

DNP-As(2,4-dinitro phenyl-coupled Ascaris extract) was prepared according to the method by Strejan et al. (J. Immunol. Vol. 98, P 893, (1967)) and by Eisen (J. Amer. Chem. Soc. Vol. 75, P 4593, (1953)) to be used as antigen. Antiserum containing HTA was prepared by the method according to Tada and Okumura (J. Immunol. Vol. 106, P 1002, (1972)) as follows: i.e. spleen was taken out from Wistar female rat weighing 180 to 200 g and several days after 1 mg of DNP-As and $1 \times 10^{10}$ of Bordetella pertussis vaccine were injected into four footpads of the rat to induce senitization. After five days, again 0.5 mg of DNP-As was solely injected into the dorsal muscles. Eight days after priming, blood was taken by paracentesis of aorta under anesthetic condition with ether and the obtained antiserum was stored at $-80°$ C.

Titer of the stored antiserum was determined by 72 hour PCA method in rat as described in the following item (2). The maximal dilution of the antiserum which can give a spot with a diameter of around 5 mm was usually 500 times.

(2) Evaluation of PCA in rat

The diluted antiserum ($\times 30$) was injected 0.05 ml/site intradermally into the shaved back of normal Wistar rat weighing 140 to 160 g. After 72 hours, 1 ml of physiological saline containing 2 mg of DNP-As and 2.5 mg of Evans blue was injected intravenously.

Test compound was dissolved in 0.5% aqueous solution of $KHCO_3$, which was administered intravenously in an amount of 2 ml/kg just before the administration of the antigen. The animal was sacrificed 30 minutes after antigen challenge and the cutis was peeled off. The intensity of PCA was evaluated for the measurment of the leaked amount of the pigment. The leaked pigment was extracted according to the method by Harada et al. (Jpn. J. Allergol., Vol. 15, P 1, (1966)) and the leaked amount was measured by spectrophotometry. Fifty % inhibitory dose for the leaked amount of the pigment was regarded as $ID_{50}$ value of the test compound. The results were shown in Table 1.

TEST EXAMPLE 2

The intraperitoneal actute toxicity test was carried out using mouse for the chromene derivatives of the present invention. Normal Slc: ddy male 4 weeks mice were preliminarily breeded for a week at a breeding room and those weighing 25 to 27 g were subjected to the test. The test compounds were used by suspending in 0.5% aqueous solution of sodium carboxymethylcellulose. Ten ml/kg was administered intraperitoneally through the right abdomen of the animal using the prescribed needle (five mice per group). The lethal dose was presumed by the observation during 14 days after administration. The results were shown in Table 1.

TABLE 1

| Test Compound | $ID_{50}$ (mg/kg) | MLD (mg/kg) |
| --- | --- | --- |
| [A] | 0.50 | >1000 |
| [B] | 0.10 | >1600 |
| [C] | 0.10 | >1500 |
| [D] | 0.16 | >1600 |
| [E] | 0.20 | >1500 |
| [F] | 0.16 | >1600 |
| [G] | 0.20 | >1500 |

REFERENCE EXAMPLE 1

[Preparation of 3-cyano-2-oxo-8-chromenyloxyacetic acid]

Ten ml of tetrahydrothiophene was cooled with ice, to which 13.4 g of pulverized anhydrous aluminium bromide was gradually added. After stirring for 5 minutes, a temperature was brought to room temperature and then a solution of 2.6 g of 3-cyano-2-oxo-8-chromenyloxyacetic acid methyl ester dissolved in 30 ml of methyl chloride was gradually added. After stirring for 2 hours, the reaction mixture was poured into a mixture of 20 ml of concentrated hydrochloric acid and 200 ml of ice water and a precipitate was filtered, which was recrystallized to give a desired compound.

Yield: 2.1 g (85.7%)
Light yellow needle crystal (isopropyl alcohol)
Melting point: 246° to 249° C.
Infrared absorption spectrum ($\nu_{max}^{KBr}$ cm$^{-1}$): 2650 to 3300, 1740, 1725 and 1610
Nuclear magnetic resonance ($CF_3 CO_2 H$)$\delta$: 4.81 (2H, s), 7.14 (3H, br s) and 8.27 (1H, s)

REFERENCE EXAMPLE 2

[Preparation of 4-(3-cyano-2-oxo-8-chromenyloxy)butyric acid]

In 25 ml of ethanol was dissolved 4.3 g of 4-(3-formyl-2-hydroxyphenyloxy)butyric acid and 1.35 g of malononitrile, to which 3 ml of an aqueous solution containing 0.12 g of potassium fluoride was added at 40° C. and the mixture was vigorously stirred for 2 minutes. Then 5 ml of concentrated hydrochloric acid was added and the mixture was stirred for 3 minutes, followed by ice-cooling. A precipitate was filtered and recrystallized to give a desired compound.

Yield: 2.6 g (47.6%)
Light yellow needle crystal (isopropyl alcohol)
Melting point: 210° to 212° C.
Infrared absorption spectrum ($\nu_{max}^{KBr}$ cm$^{-1}$): 3200 to 2500, 2250, 1750 and 1710
Nuclear magnetic resonance ($CF_3 CO_2 H$)$\delta$: 2.14 to 2.42 (2H, m), 2.75 (2H, t, J=6 Hz) and 4.17 (2H, t, J=6 Hz), 7.04 to 7.26 (3H, m) and 8.33 (1, s)
Mass spectrum (m/e): 273 (M+), 256, 214, 201, 187, 159, 115 and 87

REFERENCE EXAMPLE 2'

[Preparation of 4-(3-cyano-2-oxo-8-chromenyloxy)butyric acid]

After 10 ml of ethanol was added to 6.0 g of 4-(3-cyano-2-oxo-8-chromenyloxy)butyric acid ethyl ester, 50 ml of 2N aqueous solution of sodium hydroxide was added to the mixture and the resultant was stirred for 5 minutes at room temperature. Then the reaction mixture was poured into a mixture of 10 ml of concentrated hydrochloric acid and 200 ml of ice water and a precipitate was filtered, which was recrystallized to give a desired compound.

Yield: 4.5 g (83.0%)

The physicochemical properties of the obtained compound were agreed with those of the compound obtained in Reference Example 2.

REFERENCE EXAMPLE 3

[Preparation of 4-(3-cyano-2-oxo-6-chromenyloxy)butyric acid]

The procedures of Reference Example 2 were repeated except that 6.0 g of 4-(3-cyano-2-oxo-6-chromenyloxy)butyric acid ethyl ester was employed as a starting material to give a desired compound.

Yield: 4.4 g (81.3%)

Light yellow needle crystal (isopropyl alcohol)

Melting point: 198° to 202° C.

Infrared absorption spectrum ($\nu_{max}^{KBr}$ cm$^{-1}$): 3200 to 2500, 2250, 1745 and 1710

Mass spectrum (m/e): 273 (M+), 256, 214, 201, 187 and 159

REFERENCE EXAMPLE 4

[Preparation of 6-(3-cyano-2-oxo-8-chromenyloxy)hexanoic acid]

The procedures of Reference Example 1 were repeated except that 3.15 g of 6-(3-cyano-2-oxo-8-chromenyloxy)hexanoic acid methyl ester was employed as a starting material to give a desired compound.

Yield: 2.4 g (80.0%)

Light yellow needle crystal (isopropyl alcohol)

Melting point: 146° to 148° C.

Infrared absorption spectrum ($\nu_{max}^{KBr}$ cm$^{-1}$): 3200 to 2600, 2250, 1740 and 1700

Nuclear magnetic resonance (CF$_3$ CO$_2$ H)$\delta$: 146 to 2.08 (6H, m), 2.51 (2H, t, J=6 Hz), 4.11 (2H, t, J=6 Hz), 7.02 to 7.29 (3H, m) and 8.33 (1H, s)

Mass spectrum (m/e): 301 (M+), 208, 187, 115 and 97

REFERENCE EXAMPLE 5

[Preparation of 6-(3-cyano-2-oxo-7-chromenyloxy)hexanoic acid]

The procedures of Reference Example 1 were repeated except that 3.15 g of 6-(3-cyano-2-oxo-7-chromenyloxy)hexanoic acid methyl ester was employed as a starting material to give a desired compound.

Yield: 2.4 g (80.0%)

Light yellow needle crystal (isopropyl alcohol)

Melting point: 136° to 140° C.

Infrared absorption spectrum ($\nu_{max}^{KBr}$ cm$^{-1}$): 3200 to 2600, 2250, 1740 and 1705

Mass spectrum (m/e): 301 (M+), 208, 187, 115 and 97

REFERENCE EXAMPLE 6

[Preparation of 6-(3-cyano-2-oxo-6-chromenyloxy)hexanoic acid]

The procedures of Reference Example 1 were repeated except that 3.15 g of 6-(3-cyano-2-oxo-6-chromenyloxy)heanoic acid methyl ester was employed as a starting material to give a desired compound.

Yield: 2.3 g (87.5%)

Light yellow needle crystal (isopropyl alcohol)

Melting point: 123° to 125° C.

Infrared absorption spectrum ($\nu_{max}^{KBr}$ cm$^{-1}$): 3200 to 2600, 2250, 1740 and 1700

Nuclear magnetic resonance (CDCl$_3$)$\delta$: 1.33 to 1.85 (6H, m), 2.30 (2H, t, J=6 Hz), 3.80 (2H, t, J=6 Hz), 6.59 (1H, br s), 6.80 to 6.92 (2H, m) and 7.75 (1H, s)

Mass spectrum (m/e): 301 (M+), 208, 187, 115 and 97

REFERENCE EXAMPLE 7

[Preparation of 6-(3-cyano-2-oxo-5-chromenyloxy)hexanoic acid]

The procedures of Reference Example 1 were repeated except that 3.15 g of 6-(3-cyano-2-oxo-5-chromenyloxy)hexanoic acid methyl ester was employed as a starting material to give a desired compound.

Yield: 2.5 g (83.2%)

Light yellow needle crystal (isopropyl alcohol)

Melting point: 133° to 136° C.

Infrared absorption spectrum ($\nu_{max}^{KBr}$ cm$^{-1}$): 3200 to 2600, 2250, 1740 and 1700

Mass spectrum (m/e): 301 (M+), 208, 187, 115 and 97

EXAMPLE 1

[Preparation of [2-oxo-3-(1H-tetrazole-5-yl)-2H-chromene-8-yloxy]acetic acid]

To 80 ml of dried tetrahydrofuran cooled with ice was gradually added 5.4 g of pulverized anhydrous aluminium chloride. After stirring for 15 minutes, 7.8 g of sodium azide was added and the mixture was further stirred for 15 minutes. After a temperature of the solution was brought to room temperature, 2.5 g of 3-cyano-2-oxo-8-chromenyloxyacetic acid was added and the mixture was gradually heated to carry out the reaction under reflux for 120 hours. After the reaction was completed, the reaction mixture was poured into a mixture of 20 ml of concentrated hydrochloric acid and 300 ml of ice water to form a precipitate, which was filtered and recrystallized to give a desired compound.

Yield: 1.2 g (41.7%)

Colorless needle crystal (dioxane)

Melting point: 268° to 269° C.

Infrared absorption spectrum ($\nu_{max}^{KBr}$ cm$^{-1}$): 3300, 2500 to 3650, 1710, 1620 and 1610

Nuclear magnetic resonance (CF$_3$ CO$_2$ H)$\delta$: 4.84 (2H, s), 7.11 to 7.33 (3H, m) and 8.97 (1H, s)

Mass spectrum (m/e): 288 (M+), 279, 251, 245, 200, 187 and 149

Elementary analysis for C$_{12}$H$_8$N$_4$O$_5$ Found (%): C 49.78, H 2.91, N 19.3; Calcd.(%): C 50.00, H 2.80, N 19.44.

EXAMPLE 2

[Preparation of 4-[2-oxo-3-(1H-tetrazole-5-yl)-2H-chromene-8-yloxy]butyric acid]

The procedures of Example 1 were repeated except that 2.7 g of 4-(3-cyano-2-oxo-8-chromenyloxy)butyric acid was employed as a starting material and the reaction was carried out for 20 hours to give a desired compound.

Yield: 2.7 g (85.8%)

Colorless needle crystal (dioxane)

Melting point: 247° to 248° C.

Infrared absorption spectrum ($\nu_{max}^{KBr}$ cm$^{-1}$): 3450, 3200 to 2500 and 1735

Nuclear magnetic resonance (CF$_3$CO$_2$H)δ: 2.28 (2H, quin, 6 Hz), 2.76 (2H, t, J=6 Hz), 4.19 (2H, t, 6 Hz), 7.21 (3H, s) and 9.01 (1H, s)

Mass spectrum (m/e): 316 (M+), 299, 230, 202, 188, 174, 146, 130, 118 and 102

Elementary analysis for C$_{14}$H$_{12}$N$_4$O$_5$ Found (%): C 53.02, H 3.94, N 17.57; Calcd.(%): C 53.16, H 3.82, N 17.72.

EXAMPLE 3

[Preparation of 4-[2-oxo-3-(1H-tetrazole-5-yl)-2H-chromene-6-yloxy]-butyric acid]

The procedurs of Example 1 were repeated except that 2.7 g of 4-(3-cyano-2-oxo-6-chromenyloxy)butyric acid was employed as a starting material and the reaction was carried out for 24 hours to give a desired compound.

Yield: 2.6 g (82.8%)
Light yellow needle crystal (dioxane)
Melting point: 242° to 245° C.
Infrared absorption spectrum ($\nu_{max}^{KBr}$ cm$^{-1}$): 3450, 3200 to 2500 and 1735
Mass spectrum (m/e): 316 (M+), 299, 230, 202, 188, 174, 146 and 118
Elementary analysis for C$_{14}$H$_{12}$N$_4$O$_5$ Found (%): C 52.99, H 3.96, N 17.48; Calcd. (%): C 53.16, H 3.82, N 17.72.

EXAMPLE 4

[Preparation of 6-[2-oxo-3-(1H-tetrazole-5-yl)-2H-chromene-8-yloxy]-hexanoic acid]

The procedures of Example 1 were repeated except that 3.0 g of 6-(3-cyano-2-oxo-8-chromenyloxy)hexanoic acid was employed as a starting material to give a desired compound.

Yield: 1.9 g (55.2%)
Colorless needle crystal (dioxane)
Melting point: 239° to 240° C.
Infrared absorption spectrum ($\nu_{max}^{KBr}$ cm$^{-1}$): 3450, 3300 to 2500, 1730 and 1700
Nuclear magnetic resonance (CF$_3$CO$_2$H)δ: 1.60 to 2.10 (6H, m), 2.52 (2H, t, J=6 Hz), 4.16 (2H, t, J=6 Hz), 7.24 (3H, s) and 9.04 (1H, s)
Mass spectrum (m/e): 344 (M+), 230, 202, 187, 178, 146 and 115
Elementary analysis for C$_{16}$H$_{16}$N$_4$O$_5$ Found (%): C 55.63 H 4.81, N 16.05; Calcd.(%): C 55.81, H 4.68, N 16.27.

EXAMPLE 5

[Preparation of 6-[2-oxo-3-(1H-tetrazole-5-yl)-2H-chromene-7-yloxy]-hexanoic acid]

The procedures of Example 1 were repeated except that 3.0 g of 6-(3-cyano-2-oxo-7-chromenyloxy)hexanoic acid was employed as a starting material and the reaction was carried out for 30 hours to give a desired compound.

Yield: 2.1 g (61.0%)
Colorless needle crystal (dioxane)
Melting point: 235° to 239° C.
Infrared absorption spectrum ($\nu_{max}^{KBr}$ cm$^{-1}$): 3450, 3200 to 2500, 1730 and 1700
Mass spectrum (m/e): 344 (M+), 230, 202, 187, 178 and 115
Elementary analysis for C$_{16}$H$_{16}$N$_4$O$_5$ Found (%): C 55.68, H 4.74, N 16.18; Calcd. (%): C 55.81, H 4.68, N 16.27.

EXAMPLE 6

[Preparation of 6-[2-oxo-3-(1H-tetrazole-5-yl)-2H-chromene-6-yloxy]-hexanoic acid]

The procedures of Example 1 were repeated except that 3.0 g of 6-(3-cyano-2-oxo-6-chromenyloxy)hexanoic acid was employed as a starting material to give a desired compound.

Yield: 2.4 g (69.8%)
Light yellow needle crystal (dioxane)
Melting point: 233° to 235° C.
Infrared absorption spectrum ($\nu_{max}^{KBr}$ cm$^{-1}$): 3450, 3300 to 2500 and 1730
Nuclear magnetic resonance (CF$_3$CO$_2$H)δ: 1.53 to 2.07 (6H, m), 2.52 (2H, t, J=6 Hz), 4.07 (2H, t, 6 Hz), 7.13 (1H, br s), 7.30 (2H, br s) and 9.05 (1H, s)
Mass spectrum (m/e): 344 (M+), 230, 202, 187, 178 and 115
Elementary analysis for C$_{16}$H$_{16}$N$_4$O$_5$ Found (%): C 55.57, H 4.83, N 16.12; Calcd.(%): C 55.81, H 4.68, N 16.27.

EXAMPLE 7

[Preparation of 6-[2-oxo-3-(1H-tetrazole-5-yl)-2H-chromene-5-yloxy]-butyric acid]

The procedures of Example 1 were repeated except that 3.0 g of 6-(3-cyano-2-oxo-5-chromenyloxy)hexanoic acid was employed as a starting material to give a desired compound.

Yield: 2.0 g (58.1%)
Light yellow needle crystal (dioxane)
Melting point: 233° to 238° C.
Infrared absorption spectrum ($\nu_{max}^{KBr}$ cm$^{-1}$): 3450, 3300 to 2500 and 1730
Mass spectrum (m/e): 344 (M+), 230, 202, 187, 178 and 115
Elementary analysis for C$_{16}$H$_{16}$N$_4$O$_5$ Found (%): C 55.61, H 4.78, N 16.20; Calcd.(%): C 55.81, H 4.68, N 16.27.

EXAMPLE 8

[Preparation of sodium salt of 4-[2-oxo-3-(1H-tetrazole-5-yl)-2H-chromene-8-yloxy]butyric acid]

In 100 ml of an aqueous solution of 3.4 g of sodium hydrogencarbonate (2 times equivalent) was dissolved 6.3 g of 4-[2-oxo-3-(1H-tetrazole-5-yl)-8-chromenyloxy]butyric acid and the mixture was lyophilized to give light yellow powder of sodium salt.

Yield: 6.6 g
Melting point: 300° C.

EXAMPLE 9

[Preparation of sodium salt of 6-[2-oxo-3-(1H-tetrazole-5-yl)-2H-chromene-8-yloxy]-hexanoic acid]

The procedures of Example 8 were repeated except that 6.9 g of 6-[2-oxo-3-(1H-tetrazole-5-yl)-8-chromenyloxy]hexanoic acid was employed as a starting material to give light yellow powder of sodium salt.

Yield: 7.2 g
Melting point: not less than 300° C.

EXAMPLE 10

Ten parts by weight (hereinafter the same) of 4-[2-oxo-3-(1H-tetrazole-5-yl)-2H-chromene-8-yloxy]-butyric acid obtained in Example 2, 45 parts of corn starch, 15 parts of Avicel® (microcrystalline cellulose), 3 parts of methylcellulose and 2 parts of magnesium stearate were thoroughly mixed and the mixture was passed through a 50-mesh sieve. The obtained powder was tableted with automatic compressing machine to prepare tablets containing an active principle of 20 mg/tablet.

EXAMPLE 11

The procedures of Example 10 were repeated except that 6-[2-oxo-3-(1H-tetrazole-5-yl)-2H-chromene-8-yloxy]hexanoic acid obtained in Example 4 was employed to prepare tablets containing an active principle of 20 mg/tablet.

EXAMPLE 12

Ten parts of 4-[2-oxo-3-(1H-tetrazole-5-yl)-2H-chromene-8-yloxy]butyric acid obtained in Example 2, 55 parts of lactose, 30 parts of corn starch, 8 parts of Avicel® and 2 parts of magnesium stearate were thoroughly mixed and the mixture was filled in a gelatin capsule to prepare capsules containing an active principle of 20 mg/capsule.

EXAMPLE 13

The procedures of Example 12 were repeated except that 6-[2-oxo-3-(1H-tetrazole-5-yl)-2H-chromene-8-yloxy]hexanoic acid obtained in Example 4 was employed to prepare capsules containing an active principle of 20 mg/capsule.

EXAMPLE 14

The tablets obtained in Example 10 were crashed and the resultant was screened with a 50-mesh sieve and a 100-mesh sieve to prepare granules having a particle size of 50 to 100 mesh and containing an active principle of 50 mg/g.

EXAMPLE 15

The same mixture as in Example 12 was reduced to a powder, which was screened with a 100-mesh sieve to prepare powders having a mean particle size of 120 mesh and containing an active principle of 50 mg/g.

EXAMPLE 16

In 1000 ml of physiological saline was dissolved 2.0 g of sodium salt of 4-[2-oxo-3-(1H-tetrazole-5-yl)-2H-chromene-8-yloxy]butyric acid obtained in Example 8 and pH was adjusted to 7.4 to prepare injections.

EXAMPLE 17

In 1000 ml of distilled water was dissolved 2.0 g of sodium salt of 4-[2-oxo-3-(1H-tetrazole-5-yl)-2 H-chromene-8-yloxy]butyric acid obtained in Example 8, 0.1 g of methyl parahydroxybenzoate, 0.1 g of butyl parahydroxybenzoate and 7.5 g of sodium chloride to prepare nasal drops.

What we claim is:

1. A chromene derivative having the general formula (I):

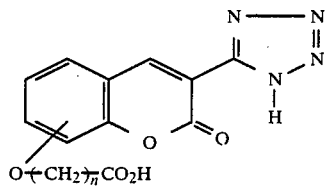

wherein n is 1 to 5 and the $-O-(CH_2)_n-CO_2H$ group is attached at 5-position, 6-position, 7-position or 8-position of the chromene ring, and pharmaceutically acceptable salts thereof.

2. The chromene derivative and pharmaceutically acceptable salts thereof as defined in claim 1, wherein the chromene derivative is [2-oxo-3-(1H-tetrazole-5-yl)-2H-chromene-8-yloxy]acetic acid.

3. The chromene derivative and pharmaceutically acceptable salts thereof as defined in claim 1, wherein the chromene derivative is 4-[2-oxo-3-(1H-tetrazole-5-yl)-2H-chromene-8-yloxy]butyric acid.

4. The chromene derivative and pharmaceutically acceptable salts thereof as defined in claim 1, wherein the chromene derivative is 4-[2-oxo-3-(1H-tetrazole-5-yl)-2H-chromene-6-yloxy]butyric acid.

5. The chromene derivative and pharmaceutically acceptable salts thereof as defined in claim 1, wherein the chromene derivative is 6-[2-oxo-3-(1H-tetrazole-5-yl)-2H-chromene-8-yloxy]hexanoic acid.

6. The chromene derivative and pharmaceutically acceptable salts thereof as defined in claim 1, wherein the chromene derivative is 6-[2-oxo-3-(1H-tetrazole-5-yl)-2H-chromene-7-yloxy]hexanoic acid.

7. The chromene derivative and pharmaceutically acceptable salts thereof as defined in claim 1, wherein the chromene derivative is 6-[2-oxo-3-(1H-tetrazole-5-yl)-2H-chromene-6-yloxy]hexanoic acid.

8. The chromene derivative and pharmaceutically acceptable salts thereof as defined in claim 1, wherein the chromene derivative is 6-[2-oxo-3-(1H-tetrazole-5-yl)-2H-chromene-5-yloxy]hexanoic acid.

9. A pharmaceutical composition which comprises:
an antiallergic effective amount of a chromene derivative selected from the group consisting of compounds according to formula (I)

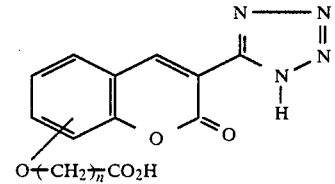

wherein n is 1 to 5 and the $-O-(CH_2)_n-CO_2H$ group is attached at the 5-position, 6-position, 7-position or 8-position of the chromene ring and the pharmaceutically acceptable salts thereof; and
a pharmaceutically acceptable carrier.

10. A pharmaceutical composition according to claim 9, wherein said chromene derivative is selected from the group consisting of 3-oxo-3-(1H-tetrazole-5-yl)-[2H-chromene-8-yloxy]acetic acid and pharmaceutically acceptable salts thereof.

11. A pharmaceutical composition according to claim 9, wherein the chromene derivative is selected from the group consisting of 4-[2-oxo-3-(1H-tetrazole-5-yl)-2H-chromene-8-yloxy]butyric acid and pharmaceutically acceptable salts thereof.

12. A pharmaceutical composition according to claim 9, wherein the chromene derivative is selected from the group consisting of 4-[2-oxo-3-(1H-tetrazole-5-yl)-2H-chromene-6-yloxy]butyric acid and pharmaceutically acceptable salts thereof.

13. A pharmaceutical composition according to claim 9, wherein the chromene derivative is selected from the group consisting of 6-[2-oxo-3-(1H-tetrazole-5-yl)-2H-chromene-8-yloxy]hexanoic acid and pharmaceutically acceptable salts thereof.

14. A pharmaceutical composition according to claim 9, wherein the chromene derivative is selected from the group consisting of 6-[2-oxo-3-(1H-tetrazole-5-yl)-2H-chromene-7-yloxy]hexanoic acid and pharmaceutically acceptable salts thereof.

15. A pharmaceutical composition according to claim 9, wherein the chromene derivative is selected from the group consisting of 6-[2-oxo-3-(1H-tetrazole-5-yl)-2H-chromene-6-yloxy]hexanoic acid and pharmaceutically acceptable salts thereof.

16. A pharmaceutical composition according to claim 9, wherein the chromene derivative is selected from the group consisting of 6-[2-oxo-3-(1H-tetrazole-5-yl)-2H-chromene-5-yloxy]hexanoic acid and pharmaceutically acceptable salts thereof.

* * * * *

UNITED STATES PATENT AND TRADEMARK OFFICE
CERTIFICATE OF CORRECTION

PATENT NO. : 4,731,375
DATED : March 15, 1988
INVENTOR(S) : Jun NAKANO et al

It is certified that error appears in the above-identified patent and that said Letters Patent is hereby corrected as shown below:

On the cover page, in the abstract, line 3, "$-(O-CH_2)_n-CO_2H$" should read -- $-O-(CH_2)_n-CO_2H$ --.

Column 1, line 51, "$-O-(CH_2)_n-CO_2H$" should read -- $-O-(CH_2)_n-CO_2H$ --.

line 57, "$(CH_2)_n-CO_2H$" should read --$(CH_2)_n-CO_2H$--.

Column 2, line 25, "$-(O-CH_2)_n-CO_2H$" should read -- $-O-(CH_2)_n-CO_2H$ --.

Column 3, lines 58 and 59, "$-(O-CH_2)_n-CO_2R$" should read -- $-O-(CH_2)_n-CO_2R$ --.

Signed and Sealed this

Eighth Day of November, 1988

Attest:

DONALD J. QUIGG

*Attesting Officer*   *Commissioner of Patents and Trademarks*